United States Patent [19]

Vandermeerssche

[11] Patent Number: 4,608,854
[45] Date of Patent: Sep. 2, 1986

[54] TEST HOLDER FOR FLAT SPECIMENS

[76] Inventor: Gaston A. Vandermeerssche, 9240 N. Sleepy Hollow La., Milwaukee, Wis. 53217

[21] Appl. No.: 688,697

[22] Filed: Jan. 4, 1985

[51] Int. Cl.⁴ ............................................. G01N 3/56
[52] U.S. Cl. ...................................... 73/7; 73/864.91
[58] Field of Search ............... 73/7, 8, 860, 432 Z, 73/432 R, 432 SD, 432 V, 432 J, 432 K, 864.91

[56] References Cited

U.S. PATENT DOCUMENTS

| 2,734,375 | 2/1956 | Galbraith et al. | 73/7 |
| 3,060,719 | 10/1962 | Pearlman | 73/7 |
| 3,134,255 | 5/1964 | Oliver, Jr. et al. | 73/7 |
| 4,507,953 | 4/1985 | Vandermeerssche | 73/7 |
| 4,529,184 | 7/1985 | Vandermeerssche | 73/856 X |
| 4,534,225 | 8/1985 | Peacock et al. | 73/864.91 X |

FOREIGN PATENT DOCUMENTS

| 519614 | 7/1976 | U.S.S.R. | 73/432 Z |
| 794419 | 2/1981 | U.S.S.R. | 73/432 Z |
| 953525 | 8/1982 | U.S.S.R. | 73/7 |
| 1015279 | 4/1983 | U.S.S.R. | 73/7 |

Primary Examiner—Stewart J. Levy
Assistant Examiner—Tom Noland
Attorney, Agent, or Firm—Quarles & Brady

[57] ABSTRACT

A holder is shown for flat specimens which are to be tested for the abrasion resistance of coatings or printed matter. In one embodiment, the holder is formed with block members with pads placed therebetween for reception of the specimens in face-to-face contact. The block members have curved surfaces at the ends to simulate the motion of transportation when utilized in conjunction with an abrasion testing machine. A retainer strap has flanges for engaging curved end portions of the blocks to aid in retaining them in contact. A method of testing flat specimens is also described.

17 Claims, 4 Drawing Figures

TEST HOLDER FOR FLAT SPECIMENS

BACKGROUND OF THE INVENTION

This invention relates to the testing of labels, and more particularly to a holder for testing the abrasion resistance of a label separately from a container as well as a method of so testing.

In my co-pending application Ser. No. 06/411,673 filed Aug. 26, 1982 and now U.S. Pat. No. 4,507,953 for "Abrasion Testing Machine", I have disclosed a machine for testing the abrasion resistance of coatings used on cans. The preferred form of the machine is capable of accepting a six-pack of cans and to subject the cans to forces and vibrations which simulate those which would be encountered during shipment. The surfaces of adjacent cans in contact rub against each other as a result of the vibrations. The testing equipment is particularly useful in testing either filled or empty beverage cans. In my co-pending application Ser. No. 06/456,577 filed Jan. 7, 1983 and now U.S. Pat. No. 4,529,184 for "Test Specimen Holder", I have disclosed a holder for testing specimens such as empty cans and particularly cans arranged in a six-pack configuration.

In addition to the testing of can surface coatings, there is a need for a device which can test the abrasion resistance of labels separately from a can surface. In particular, there is a need to test the abrasion resistance of printing and pictorial subject matter on any surface subject to abrasion such as the covers of books and catalogs, paper labels, the surfaces of shipping cartons and bags, sheet metal labels in the form of coated coil, etc. so as to be able to ascertain the reasons for possible failure.

The present invention is directed to a holder for flat specimens which will simulate their condition during transportation such as the condition of paper labels on transported filled cans and the covers of books and catalogs. The holder is particularly suited for use with my previously indicated Abrasion Testing Machine, the disclosure of which is herein incorporated by reference.

SUMMARY OF THE INVENTION

In accordance with one aspect of the invention, I provide a test specimen holder and a method of its use which includes solid block-like body members or panel holders having flat and opposed surfaces. A resilient pad member is placed on opposing panel holder surfaces and is adapted to be positioned oppositely and in contact with respect to each other. The pad members are so positioned with respect to each other to receive specimen labels in contact with each other. The panel holders have end sections a portion of which includes a curved surface for seating on a vibrating surface in a testing machine such as previously referred to in my Abrasion Testing Machine.

In accordance with another aspect of the invention, I provide a plurality of such block-like panel holders joined together in a line by a strap-like holding pad having a projection at each end which engages opposing sides of the panel holders to hold the block members in contact with each other.

In the preferred embodiment, four of the panel holder members are positioned in a row with the panel holders having an elongated eliptical shape in longitudinal cross section. The four body members are held together by a retainer strap which extends over the tops of the curved end sections of the body members and includes flange members having surfaces complementary to the surfaces of the body members. In this assembled manner, and with labels placed in a face-to-face and opposing manner between the two centered blocks, the assembled body members are readily placed in the previously referred to Abrasion Testing Machine.

It is a principal object of the invention to provide a holder for the abrasion testing of printed matter such as labels as well as a method of its use.

It is another object to provide such a holder for a label which can simulate the effects of a filled container.

It is still another object of the invention to provide such a holder which can be reused and which can be quickly and easily assembled in conjunction with the label to be tested as well as placed in an abrasion testing machine.

The foregoing and other objects and advantages of the invention will appear in the following detailed description. In the description, reference is made to the accompanying drawings which form a part hereof and which disclose preferred embodiments of the invention.

DETAILED DESCRIPTION OF THE PREFERRED EMBODIMENTS

Figure 1:
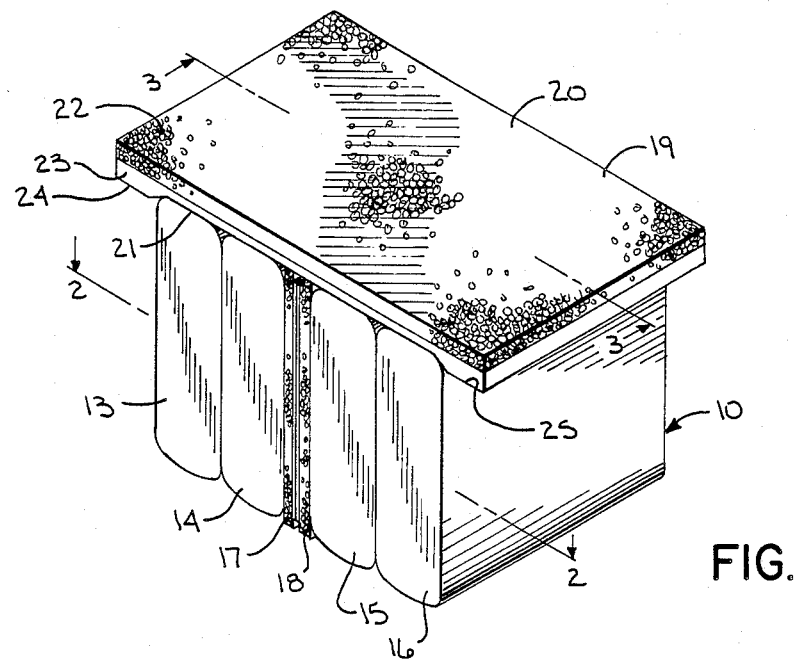
FIG. 1 is a top perspective view of the holder with four body members in place and joined together by a retainer strap.
Figure 2:
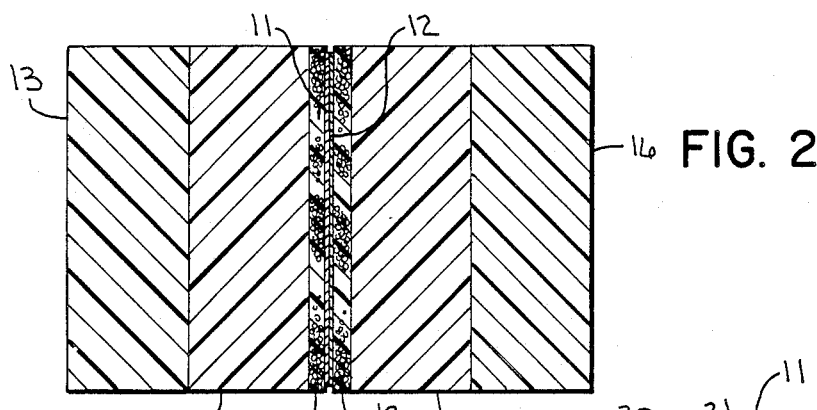
FIG. 2 is a view in horizontal section taken along line 2—2 of FIG. 1
Figure 3:
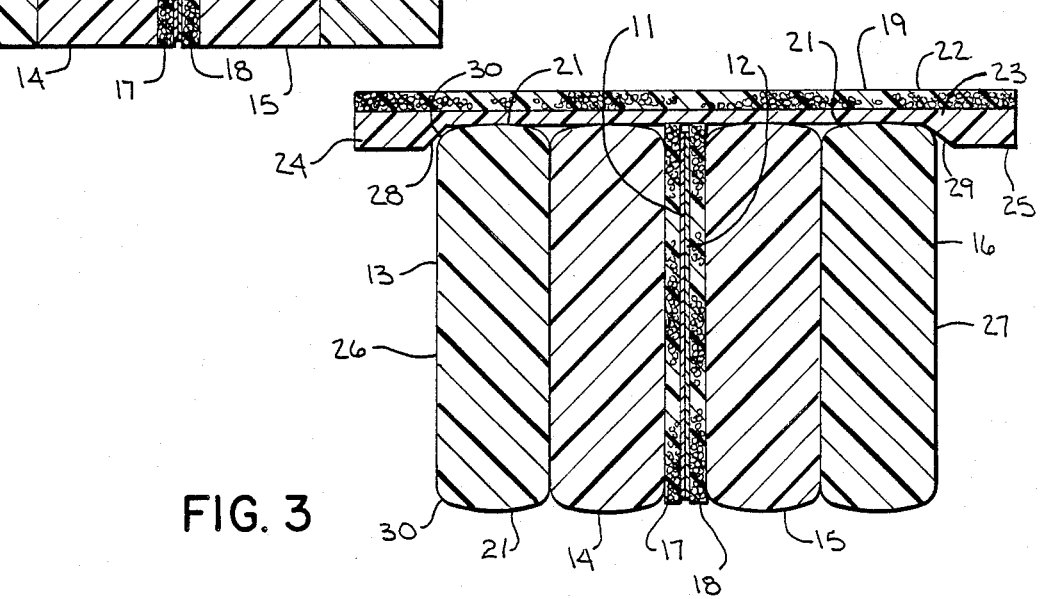
FIG. 3 is a view in vertical section taken along line 3—3 of FIG. 1.

Referring to FIGS. 1–4, the test specimen holder generally 10 is adapted to be used with the labels such as 11 and 12 which are typically formed of paper. In the preferred embodiment, the four block-like members 13, 14, 15, and 16 are aligned in a row with the blocks 14 and 15 having the pad members 17 and 18. The pad members 17 and 18 are positioned opposite to each other with the labels 11 and 12 placed therebetween in face-to-face contact. A suitable material for the pad members 17 and 18 is a polyurethane, although other natural and synthetic elastomers would be usable. At a durometer hardness of between 20 and 30, such material in conjunction with the more rigid blocks 13–16 will closely simulate the resistance of contents of a can or package in contact during shipment, as well as act to hold the labels 11 and 12 in place through a suction effect of the pad member material. The blocks 13–16 are held together for alignment purposes by a retainer strap 19 having a central portion 20 and dimensioned to extend over the top ends 21 of the blocks 13–16. The strap 19 is formed with an upper flexible panel member 22 and a lower flexible panel member 23 of the same dimension but having the projections or flanges 24 and 25 extending downwardly at the ends to partially engage a portion of the side walls 26 and 27 of the blocks 13 and 16, respectively. This is best seen in FIG. 3.

Referring specifically to FIG. 3, the flanges 24 and 25 have a straight walled surface 28 and 29 for engagement with the curved surface 30 of the panel blocks 13 and 16. It will be noted in this respect that all of the blocks 13-16 are similar in construction having end sections such as 21 with the curved shoulders or surfaces 30 of the same radius of curvature. The flanges 24 and 25 are spaced from each other a distance of 6½ inches to retain the blocks 13-16 in a compact manner and with the pad members 17 and 18 in a slightly compressed condition. In this condition, the labels 11 and 12 will likewise be held in a slightly compressed state. When in this state, the specimen holder 10 is ready for placement into my previously referred to Abrasion Testing Machine. When placed therein, the block side walls 26 and 27 will be contacted by the left and right pressure plates (39) and (40) and central portion 20 of strap 19 will be contacted with the top pressure plate (57) to hold the side walls 26 and 27 as well as strap 19 in a relatively stationary manner. The reference numerals in parenthesis in the preceding sentence and any used hereafter, reference to the incorporated disclosure of the referred to Abrasion Testing Machine.).

Figure 4:
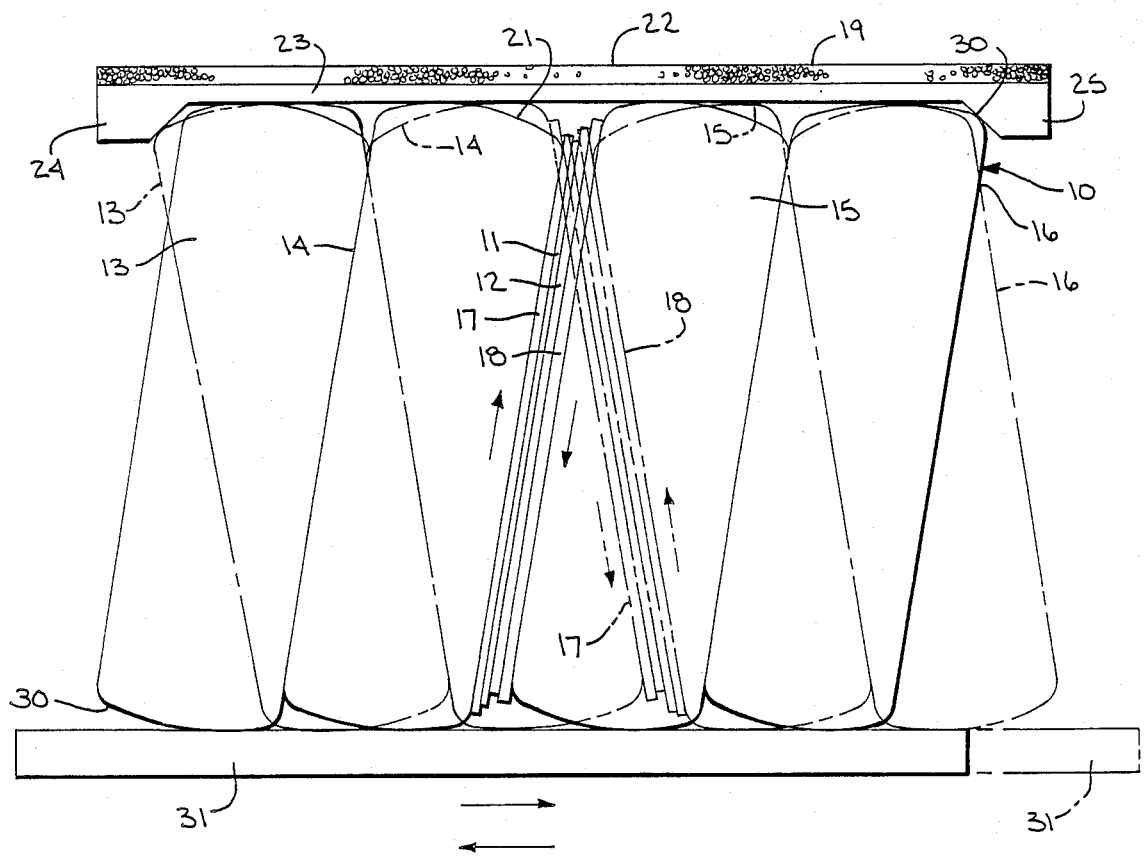
FIG. 4 is a view in side elevation illustrating the lateral motion of the holder of the present invention when placed in the preferred Abrasion Testing Machine.

Referring to FIG. 4, the movement of the panel blocks 13-16 when the Abrasion Testing Machine is activated is illustrated and its method of use is hereafter described. It will be seen that a motion similar to the transportation of cans or other packaging is imparted where the containers are subject to a swinging and swaying motion. This is effected in the present holder 10 in conjunction with the Abrasion Testing Device wherein the holder 10 is subjected to a vibrating motion by vibrating platform 31. As illustrated in FIG. 4, the back and forth motion of the panel holding blocks 14 and 15 will create a back and forth sliding action of the pad members 17 and 18 as well as a similar motion to the labels 11 and 12. This frictional motion imparted to the labels is also indicated by the directional arrows as the panel holding blocks 17 and 18 move laterally. As strap 19 is held in a permanent position by a pressure plate (57), lateral movement will be such that there is substantially the same lateral displacement of 1¼ inch at the bottom of each of the blocks 13-16. It will be further appreciated that this back and forth motion is aided by the curved surfaces 30 of the top ends 21 of the panel holding blocks 13-16 as retained by the strap flanges 24 and 25 which do not move but because of the sliding surface of lower panel 23 and flanges 24 and 25 will permit the curved end sections 21 in contact therewith to slide thereover. The amount of abrasion desired is easily selected as the length of lateral displacement or stroke is directly proportional thereto.

In the previous operational description of the holder 10, the labels 11 and 12 were subjected to abrasion testing. These labels would have the usual printing inks and coatings placed therein and would be positioned in face-to-face contact. After a predetermined time of testing an indication of abrasion resistance will be ascertained as described in conjunction with the Abrasion Testing Device. It should be pointed out that the holder 10 is not limited to testing labels wherein each have markings or coatings. Instead, a paper receptor could be substituted for one of the labels as an indicator for abrasion resistance. Alternatively, a section of a fiber or corrugated carton could be substituted as well as metal or plastic for the paper receptor as an indicator of abrasion resistance.

In the foregoing description, flat specimens were placed for testing between the pad members 17 and 18. It will be appreciated that flat specimens need not necessarily be in an original flat state but could be cut from a round object such as from a can and placed flat between pads 17 and 18. Paper labels are described for use in conjunction with the holder 10. This type of paper can be of a wide variety of types including tissue. Alternatively, cloth fabric could also be tested with the holder member 10. Neither is the test specimen holder 10 limited to testing labels. Instead, any surface having printing or pictorial subject matter which is subject to abrasion during transportation could be tested such as the covers of books and catalogs as well as the surfaces of shipping containers. The versitility of the specimen holder is seen in the fact that the printed or pictorial subject matter on a bottle closure cap could be tested by placing the cap in an opening of a flat section of polyurethane which could be substituted for pad member 17. An opposing cap could be similarily positioned in place of pad member 18 with the caps in contact with each other or a receptor substituted as previously indicated. In this instance the flat section of polyurethane would have a durometer of between 40-45. Neither is the holder member limited to testing printing or pictorial matter. The surface wear of printing plates can be determined by placing the plates in contact with each other between the blocks such as 14 and 15.

The panel holder members 13-16 will measure 5 inches in height, 4⅞ inches in depth and will be 1 9/16 inches in width. They will have a durometer of between 80-90 and are preferably fabricated from a polyurethane material. If desired, other semirigid materials such as hard rubber or wood could be substituted. The pad members 17 and 18 are a ¼ inch in thickness and cover substantially all of the flat adjacent surfaces of the panel holder blocks 14 and 15. They are also preferably formed of a polyurethane composition. Alternatively, rubber or other sponge-like plastic compositions could be used instead with the provision that desired resiliency and retention of the specimens be obtained. While the pad members 17 and 18 are fabricated separately from the blocks 14 and 15, they could be formed integrally, if desired. The strap 19 is depicted as having an upper flexible panel 22 formed from a plastic foam material such as polyurethane with a lower panel 23 and the integral flanges 24 and 25 formed from a more rigid but flexible material. The lower panels and flanges are preferably formed from polyurethane however other materials such as rubber or aluminum could be used with the provision that they provide the previously described sliding surface. Further, the strap 19 could be formed from a single composite but laminated polyurethane material. It should be further stated that flanges 24 and 25 extend outwardly from lower panel 23 at a 45° angle. They will preferably have a ⅜ inch extension from panel 23 as measured perpendicularly thereto as well as measuring ⅜ inch across the face thereof.

Curved surfaces 30 of the panel holder blocks 13-16 have been depicted as being relatively short in dimension and have a radius of curvature for a circle with a 5 inch diameter. These surfaces could be of a larger or smaller dimension as well as have a smaller or larger radius of curvature without departing from the scope of the invention. The only requirement in geometric configuration is that the previously described motion be effected to simulate the motion of transportation in a truck or railcar when placed in a testing machine.

In one embodiment, the labels 11 and 12 were placed between the pad members 17 and 18 and the blocks 14 and 15. If desired additional and simultaneous testing could be effected by placing test specimens between the blocks 13 and 14 as well as 15 and 16 in a similar manner. Further to aid in the sliding action of the blocks 14–16 and in the instance where specimens are not placed therebetween, sliding panels such as steel plates could be placed therebetween.

I claim:

1. A holder for flat test specimens, comprising:
   a first and a second body member defining substantially flat and opposed surfaces; and
   first and second resilient pad members operatively associated with said body member surfaces and adapted to be positioned oppositely with respect to each other with a flat specimen therebetween;
   said first and second body members having end sections, a portion of which includes opposing curved surfaces for contact with a moveable platform.

2. The holder in accordance with claim 1 wherein said body members are defined by solid block members.

3. The holder in accordance with claim 2 wherein said block members have an elongated eliptical shape in longitudinal cross section.

4. The holder in accordance with claim 1 wherein said pad members are formed of an elastomer having a hardness of between about 20 and 30 durometer.

5. The holder in accordance with claim 1 wherein said pad members are initially formed separately from said body members.

6. The holder in accordance with claim 1 wherein said pad members are dimensioned to cover substantially all of said flat surfaces of said first and second body members.

7. A holder kit for assembly of a plurality of body members for testing flat specimens comprising:
   at least two body members defining substantially flat and opposed surfaces;
   first and second resilient pad members operatively associated with said body member surfaces and adapted to be positioned oppositely with respect to each other with a flat specimen therebetween;
   said first and second body members having end sections, a portion of which includes opposing curved surfaces for contact with a moveable platform;
   a retainer strap including at least two depending projections constructed and arranged to engaged opposing sides of said body members to hold together said body members with said pad members in contact with each other.

8. A kit in accordance with claim 7 wherein said retainer strap is defined by a flexible panel member extending over the end sections of said body members.

9. A kit in accordance with claim 8 wherein said depending projections are defined by flange members having flat surfaces.

10. A kit in accordance with claim 9 wherein said body members are represented by at least four body members and said flexible panel member extends over the end sections of said body members.

11. A kit in accordance with claim 10 wherein said body member are defined by solid block members formed of a polyurethane material and have an elongated eliptical shape in longitudinal cross section.

12. A method of testing flat specimens for abrasion resistance of coatings or printed material comprising:
    placing at least two flat specimens or a flat specimen and a flat receptor between two block-like members having flat opposing surfaces and curved ends;
    positioning said block-like members on said curved ends with said flat specimens or said flat specimen and said flat receptor placed therebetween and in a face-to-face and frictional relationship; and
    imparting a back and forth motion to said block-like members with the lateral movement of said blocks at bottom portions thereof being substantially the same.

13. The method of claim 12 wherein said flat specimens are represented by paper labels.

14. The method of claim 12 wherein said back and forth motion is effected by holding outside side portions of said blocks in a relatively stationary manner while moving the bottom portions and effecting limited movement of the top portions.

15. The method of claim 14 wherein said movement at the bottom portions of said blocks is effected by lateral vibration.

16. The method of claim 15 wherein said flat specimens or said flat specimen and said receptor are supported on said block-like members by resilient pad members.

17. The method of claim 12 wherein two additional block-like members having the same configuration as said two block-like members are positioned and aligned at the sides of said block-like members opposite said specimens or said receptor and all four of said block-like members are subjected to said previously defined motion.

* * * * *